US012076675B2

(12) United States Patent
Ruszkowski et al.

(10) Patent No.: US 12,076,675 B2
(45) Date of Patent: Sep. 3, 2024

(54) AIR FILTER INACTIVATION OF VIRUSES AND MICRO-ORGANISMS

(71) Applicants: John Ruszkowski, Michigan City, IN (US); Terry Garris, Laporte, IN (US); Gregory Barker, Wanatah, IN (US)

(72) Inventors: John Ruszkowski, Michigan City, IN (US); Terry Garris, Laporte, IN (US); Gregory Barker, Wanatah, IN (US)

( * ) Notice: Subject to any disclaimer, the term of this patent is extended or adjusted under 35 U.S.C. 154(b) by 475 days.

(21) Appl. No.: 16/974,425

(22) Filed: Jan. 27, 2021

(65) Prior Publication Data
US 2022/0233981 A1 Jul. 28, 2022

(51) Int. Cl.
*B01D 39/16* (2006.01)
*A61L 2/232* (2006.01)
*A61L 2/235* (2006.01)
*F24F 13/28* (2006.01)

(52) U.S. Cl.
CPC .......... *B01D 39/1623* (2013.01); *A61L 2/232* (2013.01); *A61L 2/235* (2013.01); *F24F 13/28* (2013.01)

(58) Field of Classification Search
CPC ... D04H 3/16; B01D 46/0028; A61L 2209/14; C09D 157/08
See application file for complete search history.

(56) References Cited

U.S. PATENT DOCUMENTS 1,363,097 A * 12/1920 Duncan .................. A63G 11/00 472/112
2,706,701 A * 4/1955 Beller ...................... C08K 3/26 424/78.25
5,091,102 A * 2/1992 Sheridan .............. C11D 17/049 424/404
6,375,886 B1 * 4/2002 Angadjivand ..... D04H 1/43838 264/460
8,546,619 B2 * 10/2013 Oren ..................... C07C 201/10 568/946
9,802,187 B2 * 10/2017 Fu .......................... B01J 35/023
2017/0312673 A1 * 11/2017 Smith .................. B01D 46/023
2020/0299881 A1 * 9/2020 Ashraf .............. A61F 13/15707
2021/0158987 A1 * 5/2021 Johnson ................... H05H 6/00
2021/0171883 A1 * 6/2021 Hara .................... C11D 3/3749

FOREIGN PATENT DOCUMENTS

CN 103025833 A * 4/2013 ............. A01N 25/08
CN 104619901 A * 5/2015 ......... B32B 38/0036
DE 19930979 A1 * 1/2001 ......... B01D 39/1623
NO 311007 B1 * 10/2001 ............... A61F 2/28

* cited by examiner

*Primary Examiner* — Chester T Barry

(74) *Attorney, Agent, or Firm* — Ryan M. Fountain

(57) ABSTRACT

A process is provided for removing viruses and micro-organisms from building air by inactivation of those biological elements within an HVAC filter having exuding halogenated material therein. The filter for the HVAC systems has the exuded halogenated material applied with a tackified material via a sequential spraying operation prior to heat curing either of those materials. The filter can subsequently be formed with other laminated materials for increased efficiency, and pleated for use in the HVAC system. Both porous and non-porous substrate fibers can serve as the substrate web for the exuded halogenated material, preferably processed as a non-woven web during air filter fabrication.

11 Claims, 1 Drawing Sheet

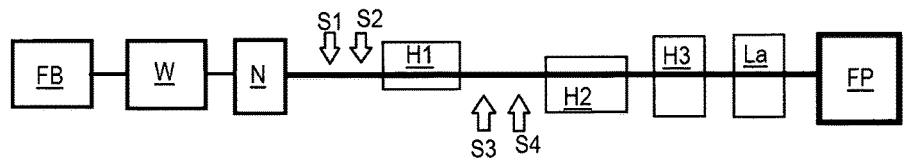

AIR FILTER INACTIVATION OF VIRUSES AND MICRO-ORGANISMS

BACKGROUND OF THE INVENTION

The present invention relates generally to HVAC systems, and more particularly, to remediation of biological contaminants in breathable air used in occupied structures.

Prior HVAC systems have been generally used to provide filtered air to buildings and the like. Unwanted viral and microbial populations entrained in such air can be a health hazard, either directly through respiratory infection or tissue contact with building occupants, or indirectly through contamination of products made and/or used in such buildings which later come into contact with persons outside of the building. Prior HVAC systems have been suggested to attempt to remove such biological health hazards, but such systems have not been as effective as desired for a variety of reasons, particularly when dealing with COVID-19 situations.

Further, this invention relates to manufacturing processes for HVAC filters. Previously, it has been known to use non-woven fibers in such filters and to treat such fibers with various chemicals and materials. However, such treatments have been limited by the chemical natures of the materials used because, for example, certain chemicals cannot be mixed together for combined application to the fibers without adverse chemical interactions.

OBJECTIVES OF THE INVENTION

Accordingly, a primary objective of the invention is to provide improved HVAC filtration and processes for making air filters. These improvements include providing such filtration and filters which:

a. are less inexpensive to manufacture, install, and maintain, b. reduce biological contamination in the processed air, c. provide filter versatility, d. accommodate a variety of different pre-existing air filtration systems, and e. increase user convenience and safety.

SUMMARY OF THE INVENTION

These and other objectives of the present invention are achieved by the provision of a process for removing viruses and micro-organisms from building air by inactivation of those biological elements within an HVAC filter having exuding halogenated material therein. The filter for the HVAC systems has the exuded halogenated material applied with a tackified material via a sequential spraying operation prior to heat curing either of those materials. The filter can subsequently be formed with other laminated materials for increased efficiency, and pleated for use in the HVAC system. Both porous and non-porous substrate fibers can serve as the substrate web for the exuded halogenated material, preferably processed as a non-woven web during air filter fabrication.

Other objects, advantages, and novel features of the present invention will become readily apparent from the following drawings and detailed description of certain preferred and alternative embodiments.

BRIEF DESCRIPTION OF THE DRAWING

FIG. 1 shows schematically the process for creation of a preferred air filter for use in the process of the present invention.

DETAILED DESCRIPTION OF PREFERRED EMBODIMENTS

The present invention provides for inactivation of viruses and micro-organisms by inactivation of those contaminants in the air filter apparatus of a HVAC system for a building or like structure, whether fixed or mobile. This invention is suitable for use in a wide variety of conventional HVAC systems, but particularly where non-woven fibrous air filter materials are used to filter the output air. Exuding halogenated material is applied to those air filter materials, together with a tackified emulsion, to contact with and retain the undesired contaminants within the air filter. The specific chemicals selected for use in the exuding halogenated material and the tackified emulsion will, preferably also inactivate the specific contaminants of concern, such as COVID-19.

With reference to FIG. 1, a preferred process for creating the air filter is to select a plurality of suitable fiber types, such as two or three Auriga or Stein fiber types of 1.5 to 2 inches, and blend the fibers together at Stage FB. Thereafter, the fibers can be blended and pre-opened in the usual manner, such as with a VO K mixer and Garrett/MTO apparatus at Stage W to create the form of the desired web. Thereafter, any desired needling can be done, such as by a Hunter Board, at stage N.

At that point, the web is ready for sequential "wet spraying" at Stages S1 and S2 to applying first the tackified emulsion and then the exuding halogenated material to the top side of the web. An example of such an emulsion would be commercially available BASF surfactant LF711. An example of such an exuding halogenated material would be Brominated Vegetable Oil. Preferably, Stage S1 sprays the material with sufficient pressure and volume as to drive that emulsion down thoroughly into the web. Thereafter, and prior to allowing the emulsion to fully dry, Stage S2 applies the material with sufficient pressure and volume that it is deposited as a surface layer to the web. The specific materials used at Stages S1 and S2 can be adapted to target specific contaminants of particular concern for a given application of the present invention.

At that point, the web is subjected to heat curing, at least on its top side. The curing preferably occurs at a temperature between 240 and 350 degrees F. and for a duration of 30 to 60 seconds as the web is moved through the heating area, H1. Thereafter, a similar spray process is applied to the opposite or underside of the web at Stages S3 and S4, using the same respective spray materials, unless it is preferred to sensitize the web to different types of contaminants on that side of the web. Alternatively, the back side of the web can be treated with a binder spray-on material or the like to assist in laminating other layers to the web, in a given application, according to conventional processes. Subsequent heat treating stages H2 and H3 are applied to the web, as needed for particular formulations of the subsequent spraying Stages S3, S4 and the like. After heat treatment, any desired laminating and/or final processing, such as pleating, cutting, folding, printing, or the like of the web, can be implemented, as indicated as Stages La and FP, such that the web is preferably formed and dimensioned as an air filter of conventional size and shape for placement into conventional HVAC systems or any desired subsequent HVAC system.

After this specially treated air filter is so produced, it is preferably installed into a HVAC system which provides for air filtration at a MERV (Minimum Efficiency Reporting Value test method ASHRAE 52.2, 2017) of between 9 and 20. During operation of that HVAC, contaminated air is passed through that air filter, thus completely the process of the present invention.

Although the present invention has been shown and described herein with respect to certain preferred embodiments and alternative configurations, those were by way of illustration and example only. For example, in especially preferred embodiments, the heat treatment of the web can be provided by a multi-pass oven. Also, while sequential spraying stages are shown above for application of the two "wet" materials, the present invention expressly contemplates that these materials can also be applied via dip coating and curtain coating to the web. Further, while a web of fibrous, non-woven material is discussed above as a suitable substrate for these materials, the present invention contemplates that other substrate materials can be similarly employed as needed for given applications. Further still, while polyester fibers have been described above or the web, the present invention contemplates use of fibers formed from other materials, as needed for given applications. Accordingly, the spirit and scope of the present invention is intended to be limited only by the terms of the appended claims.

What is claimed is:

1. The process of inactivation of viruses and micro-organisms comprised of the steps of:
   first, applying exuding halogenated material to an air filter,
   second, passing air having viruses or micro-organism entrained therewith through said air filter.

2. The process according to claim 1 wherein said air filter comprises a non-woven fibrous material constructed for use in an HVAC system.

3. The process according to claim 2 wherein said non-woven fibrous material is formed as a web from a blend of multiple types of different polyester fibers.

4. The process according to claim 3 wherein said first step includes a first phase of sequentially spraying a tackified emulsion to said web, followed by spraying said exuding halogenated material to said web, without allowing said tackified emulsion to first completely dry.

5. The process according to claim 4 wherein said first step includes a second phase of heating said web after both of said spraying is complete to cure the coatings.

6. The process according to claim 5 wherein said heating occurs between 250 and 350 degrees F. for a period of time between 30 and 60 seconds.

7. The process according to claim 3 wherein said tackified emulsion is sprayed at sufficient pressure and volume to substantially drive that media down into said web, and said exuding halogenated material is sprayed as sufficient pressure and volume to substantially deposit that media as a surface layer to said web.

8. The process according to claim 3 wherein:
   said first phase is applied first to the first side of said web, and then at least that side of the web is heated to between 240 and 350 degrees F. for a period of time between 30 and 60 seconds,
   and then the opposite side of said web is sprayed and heat treated in the same manner.

9. The process according to claim 8 wherein said web is subsequently heat treated in the same manner to the first side of said web.

10. The process according to claim 3 wherein:
    said first phase is applied first to the first side of said web, and then at least that side of the web is heated to between 250 and 350 degrees F. for a period of time between 30 and 60 seconds,
    and then the opposite side of said web is sprayed with a surface binder,
    and then said opposite side is joined with a laminate material.

11. The process according to claim 10 wherein first phase subsequently includes the step of pleated said web material for assembly into a component for use in an HVAC system for air filtration between MERV 9 to MERV 20.

* * * * *